United States Patent [19]

Barker

[11] 4,299,120

[45] Nov. 10, 1981

[54] METHOD FOR DETERMINING PLANE STRAIN FRACTURE TOUGHNESS OF NON-ELASTIC FRACTURE MECHANICS SPECIMENS

[75] Inventor: Lynn M. Barker, Salt Lake City, Utah

[73] Assignee: Terra Tek, Inc., Salt Lake City, Utah

[21] Appl. No.: 21,463

[22] Filed: Mar. 19, 1979

[51] Int. Cl.$^3$ .......................... G01N 3/08; G01N 3/32
[52] U.S. Cl. ......................................... 73/87; 73/799
[58] Field of Search ................... 73/87, 783, 799, 805, 73/806

[56] References Cited

U.S. PATENT DOCUMENTS 4,116,049  9/1978  Barker .

Primary Examiner—S. Clement Swisher
Attorney, Agent, or Firm—M. Reid Russell

[57] ABSTRACT

The present invention involves a new method for measuring plane strain fracture toughness ($K_{Ic}$) of a somewhat non-elastic material uniquely suitable for use on specimens that are smaller than have formerly been required for performing valid $K_{Ic}$ tests. The present invention involves selecting a short-rod specimen configuration in which the specimen material at a crack front or tip therein would be constrained during loading to a plane strain state and, from the measurement and anelastic analysis of a load-displacement curve that includes at least two unloading slopes the energy per unit crack area that is required to slowly advance a steady state crack can be determined, which data, along with measurement of the critical load when the crack passes through a known location, and considering the specimen geometry, is used to determine the fracture toughness, $K_{Ic}$, of the specimen.

9 Claims, 8 Drawing Figures

| Specimen Diameter (mm) | No. of Tests | Average $K_Q$ (MPa$\sqrt{m}$) | Average p | Average $K_{Ic}$ (MPa$\sqrt{m}$) | Standard Deviation |
|---|---|---|---|---|---|
| 12.7 | 2 | 27.8 | .21 | 34.5 | 1.4% |
| 22.0 | 4 | 30.2 | .12 | 34.1 | 3.0% |
| 38.1 | 7 | 31.0 | .056 | 32.5 | 4.5% |
| 63.5 | 4 | 33.1 | .047 | 34.7 | 2.8% |

METHOD FOR DETERMINING PLANE STRAIN FRACTURE TOUGHNESS OF NON-ELASTIC FRACTURE MECHANICS SPECIMENS

BACKGROUND OF THE INVENTION

1. Field of the Invention

This invention relates to a new method for measuring fracture toughness of a somewhat non-elastic specimen that is smaller in size than has heretofore been required to perform a valid $K_{Ic}$ test.

2. Prior Art

It is characteristic of our times that the strength of materials from which the machines of our technology are formed are becoming ever more critical in machine design. Particularly with regard to such things as the drilling of deep wells to tap the hydrocarbon resources of the globe, the materials from which drill bits and the cutting surfaces therefore has become increasingly critical to the tools' operations. Such metals must withstand the great temperatures, pressures, and stresses underground and afford a driller with a maximum life to minimize the cost and time involved in pulling a drill string to replace a bit. Other examples of a clear and present need for providing accurate and useful materials testing data are readily apparent in the aerospace industry, and the like.

For the past two decades, various apparatus and techniques have been proposed and developed for determining the fracture toughness characteristics of ductile and brittle materials. The present invention builds upon this technology to provide a simplified technique for measuring fracture toughness of sizes of specimens that heretofore were not appropriate for such testing procedures. Specifically, the present invention builds on an earlier patent by the present inventor entitled, "Method For Measuring Plane Strength Fracture Toughness", U.S. Pat. No. 4,116,049, issued Sept. 25, 1978. As with the method of this cited patent, the present invention depends upon keeping a steady state crack tip configuration and utilizes a maximum plane strain loading whereat, at a known or measured location, a critical fracture will occur useful in computation of the $K_{Ic}$ for such specimen. The present invention, distinct therefrom however, is not restricted to larger specimens as called for in ASTM E 399-74, but rather can produce accurate test results for elastic-plastic specimens that are much smaller in size than would formerly have been required for a performance of a valid ASTM $K^{Ic}$ measurement. Specifically, the present invention provides for obtaining an accurate fracture toughness $K_{Ic}$ measurement of certain sizes of specimens that heretofore were appropriate for elastic-plastic fracture parameter testing based on a J integral method, or $J_{Ic}$, only, which test procedure is much more complicated than that of the present invention, and therefore, the method of the present invention is a significant improvement thereover.

Like the earlier cited patented method of the present inventor for measuring plane strain fracture toughness, the present method also involves calculating the stress intensity factor or fracture toughness, $K_{Ic}$, mathematically considering the critical load applied to the specimen, the specimen size and geometry, optionally, takes into account Poisson's ratio for the specimen material, and does not require comparison of test results with tests of standard specimens, or the like. Distinct from my earlier process, the present method can be used on smaller specimens than heretofore were appropriate as the test results therefrom do not depend on the specimen exhibiting perfectly elastic characteristics. Rather, the present method allows and provides for the occurrence of plasticity or anelastic behavior around the tip of the crack in the specimen. Plasticity, of course, is the drawback to prior fracture toughness testing methods as, particularly with small specimens, it cannot generally be ignored.

The present method, unique from the cited prior patent method, involves obtaining a steady stage fracture after initial crack growth and employs at least two unloading sequences or cycles whereby, after the fracture is initiated and has progressed through or past a critical point, the specimen loading is removed, and the specimen relaxes along a straight load-displacement line. Thereafter, by re-loading the specimen and again relaxing it, after further crack extension, an area under the crack extension curve, between load-displacement lines, is produced indicative of the work done to advance the crack between the two points. This data, along with measurements of specimen compliance and taking into account specimen geometry, can be used to derive the specimen fracture toughness, $K_{Ic}$. This derivation, where the specimen does not exhibit perfect elasticity, allows for anelastic behavior in the specimen that prohibits a return of the specimen sides to their original configuration when the load is removed.

The present method, similar to the earlier patented method of the present inventor, provides a simplified and yet accurate technique for measuring fracture toughness of specimens and, as will be elaborated on later herein, has been used in a laboratory setting to produce acceptable measurements of 6061-T651 aluminum alloy specimens having only a 12.7 millimeter diameter, a much smaller diameter of specimen than could formerly by used to produce a valid $K_{Ic}$ test by my earlier patented method.

Within the knowledge of the inventor, the method of the present invention is unlike any heretofore known and is a significant improvement in the art as it provides for a simplified testing technique for use on specimens that have not heretofore been proper subjects to test for plane strain fracture toughness, and the present method is therefore believed to be both novel and unique and a significant improvement in the art.

SUMMARY OF THE INVENTION

A principal object of the present invention is to provide a method for accurately measuring plane strain fracture toughness ($K_{Ic}$) of smaller size of specimens than has heretofore been appropriate for performing valid $K_{Ic}$ testing on by prior methods.

Another object of the method of the present invention is to provide a simpler test method for measuring the plane strain fracture toughness of a specimen that does not exhibit perfect elasticity than has heretofore been possible.

Still another object of the method of the present invention is to provide a method for measuring the plane strain fracture toughness of a specimen that involves testing of a single specimen only, which method does not require a comparison of test results against a standard specimen, an accurate determination of specimen fracture toughness requiring only knowledge of the specimen geometry, specimen size, Poisson's ratio, and provides for an accurate derivation of fracture toughness even if the specimen does not exhibit perfect elasticity.

Practicing the method of the present invention for determining plane strain fracture toughness of a specimen first involves preparation of a suitable configuration of test specimen that will, when appropriately loaded, crack at a pre-determined point or line, with that crack then proceeding along a predetermined path through the specimen during continued loading. During such procedure, crack growth should be essentially stable throughout the loading cycle and, at some point or location in the specimen, there exists a point whereat, from that point, the crack will continue through the specimen with decreasing loading. The specimen for use in practicing the present method should be loaded such that loading conditions at the tip or front edge of the crack will be primarily in plane strain. Such testing should be accomplished in a stiff machine where, when a loading force reaches a maximum or peak load, that loading force can be reduced to allow the fracture to continue in a slow, steady fashion. A preferred specimen configuration is shown in my aforesaid United States Patent that involves slotting the specimen longitudinally to leave a remainder "v" therein, the apex of that "v" centered with respect to the specimen sides, which specimen is arranged to be loaded such that loading will be in plane strain across the slot.

The method of the present invention involves subjecting the above-described specimen to a plane strain loading across the specimen normal to the plane of the "v" until a crack or fracture initiates at the apex thereof. Loading is preferably provided by a stiff machine whereby loading can automatically be decreased as a fracture or crack passes through a critical location in the specimen, determining critical load for the specimen with further fracturing thereof occurring generally at a lesser load, so as to provide a steady state crack growth through the specimen. The critical crack location is a constant for a given specimen geometry and loading configuration. The critical crack length is reached at the time of the peak load and is independent of the specimen material so long as the specimen behaves according to linear elastic fracture mechanics (LEFM) principles. The peak load, of course, occurs when the crack passes through that critical crack location and, assuming linear elastic fracture mechanics principles are appropriate, with the specimen of sufficient size to provide good data, the fracture toughness or $K_{Ic}$ can be determined from the method and formulas of my prior United States Patent cited hereinabove. However, where a specimen is not sufficiently large, compared to the anelastic zone around the crack tip, it will not necessarily behave according to linear elastic fracture mechanics principles. The present method provides for determining fracture toughness by a determination of the amount of anelastic behavior, hereinafter referred to as plasticity, exhibited by the specimen along with the load required to advance the crack when the latter is at a known or measured crack length.

Practicing the method of the present invention involves establishing the specimen in a plane strain loading condition such that forces applied thereon will be across the slot therein and recording graphically the load vs. increased opening across the slot. The loading path consists initially of a linear elastic slope with the onset of non-linearity signifying the initiation of a crack at the point of the "v" remainder. Loading is increased until a steady state crack tip configuration is obtained. In a graphic representation, after a steady state is attained, then the load is removed from the specimen, and, providing no crack growth occurs on unloading, the unloading path will approximate a straight line back to the origin. This path back to the origin at unloading, of course, assumes that only elastic deformation has occurred. Therefrom, the specimen is reloaded, the loading providing a steady state quasistatically advancing crack tip that opens an additional crack length increment. Thereafter, the specimen is again unloaded and, again assuming only elastic deformation has occurred, the unloading path would again be a straight line back to the origin. The additional irrecoverable work done in advancing the crack between the two unloadings would be the area beneath the curve between the two unloading paths. From the specimen compliance, defined as the inverse slope of the unloading path, the crack length can be determined from a compliance vs. crack length calibration curve. Therefore, by determining the crack length at each unloading path as by measuring each unloading compliance, the additional crack surface area between the two unloadings can be found from a knowledge of the specimen geometry. The fracture toughness can then be calculated from the ratio of the above-mentioned irrecoverable work to the above-mentioned additional crack surface area, plus, optionally a consideration of the Poisson's ratio for the material.

However, in practice, and particularly with specimens smaller than a certain minimum size, which size depends on the material properties, it has been found that a graph of a loading path, when the load is removed from the specimen, will not return to the origin. Rather, some flexure of the specimen will be retained, which condition is due to a finite non-elastic deformation occurring around the crack front or tip during loading. Further loading to move the crack an additional distance through the specimen also results in additional non-elastic deformation with the unloading load displacement path terminating at a larger residual displacement than the first unloading path intercept. The difference in residual displacements divided by the displacement difference between the two unloading paths at the average load during the crack advance between unloadings equals the specimen "plasticity", a term defined for the purpose of applying the method of this patent. Therefrom, and taking into account the crack advance derived from the change in specimen compliance between unloadings, the work per unit area swept out by the crack front is calculated, which is the specimen material constant, $G_{Ic}$. Thereafter, applying a linear elastic fracture mechanics translation to $G_{Ic}$, the material fracture toughness, or critical stress intensity factor, $K_{Ic}$, can be determined. In practice it has been found that as the specimen plasticity may vary with the crack length, best results are obtained where the two unloading points bracket the point corresponding to the linear elastic fracture mechanics critical crack location.

As detailed hereinabove, the present method makes possible a determination of the fracture toughness of sizes of specimens that heretofore have been considered to be too small to produce accurate linear elastic fracture mechanics results taking into account the non-elastic deformation of that specimen at the crack front.

Further objects and steps in practicing the method of the present invention will become more apparent from the following detailed description taken together with the accompanying drawings.

THE DRAWINGS

FIG. 1, a profile perspective view of a slotted short rod specimen formed of a material that is suitable for use in practicing the method of the present invention, a longitudinal slot is shown formed therein with broken lines showing a preferred V-shaped remainder portion, with a crack shown as a shadowed area extending from the "v" apex into that remainder portion, with a plane strain loading force applied across the specimen shown as arrows "F";

FIG. 2, a top plan sectional view of the specimen of FIG. 1 showing the crack having advanced a distance $\Delta a$ into the V-shaped remainder portion under plane strain loading;

FIG. 3, a side elevation view of the specimen of FIG. 1 showing the crack having advanced the distance $\Delta a$ as shown in FIG. 2;

FIG. 4, a graph depicting specimen loading versus load point opening, a broken line identified as $\overline{F}$ indicating the average loading between points A and B, producing an average load point opening of $\Delta X$, and showing the unloading paths between points A and B as traveling back to a point of origin, the graph illustrating that the specimen, when unloaded, exhibits linear elastic fracture mechanics characteristics, the specimen halves returning to their original attitudes when the load is removed, the area in triangle AOB being the irrecoverable work done in advancing the crack a distance of $\Delta a$;

FIG. 5, a side elevation view of a specimen like that of FIG. 1 only showing, in broken lines, a non-elastic zone whereat the specimen would exhibit a non-linear anelastic characteristic, anelastic deformation occurring around the crack tip during loading;

FIG. 6, a graph like that of FIG. 4 only illustrating that when a specimen, like that of FIG. 5, is unloaded from points A and B the unloading path does not return to origin, but rather returns to points C and D, a distance $\Delta X_O$ therebetween, indicating a residual deformation in the specimen;

FIG. 7, a graph of experimental data produced from one test of a 22 millimeter diameter 6061-T651 aluminum specimen graphing load vs. the specimen mouth opening showing three unloading paths extrapolated back to the zero-load line; and FIG. 8, a table summarizing fracture toughness experiments like that shown in the graph of FIG. 7 and material properties of specimens machined from a single rolled drawn rod of 6061-T651 aluminum, the fracture toughness $K_{Ic}$ shown therein derived from practicing the method of the present invention.

DETAILED DESCRIPTION

Figure 1:
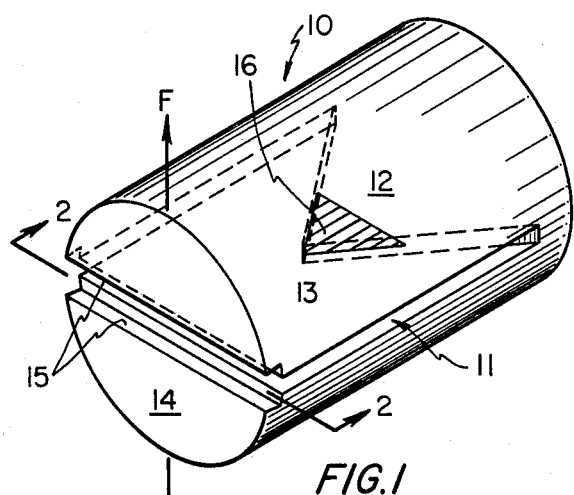

Referring now to the drawings:

Background

Heretofore, the performance of valid fracture toughness or critical stress intensity factor testing on a material has entailed performance of that testing on a specimen of that material that has dimensions or geometry above a minimum size for short-rod specimens. A preferred test procedure and specimen configuration for performing such tests on specimens larger than a minimum size is taught in my cited U.S. Pat. No. 4,116,049 entitled "Method For Measuring Plane Strain Fracture Toughness". The preferred specimen configuration shown therein is like a specimen 10 shown in FIG. 1, and is preferred for use in practicing the method of the present invention, which specimen 10 has been slotted at 11 leaving a V-shaped remainder 12 therein. Practicing the method of the present invention, like my earlier patented method, involves subjecting the specimen 10 to a plane strain loading across slot 11, as by a stiff machine, that stiff machine loading indicated or represented by arrows F, in FIG. 1.

The present invention in its practice preferably utilizes the same slotted short-rod specimen configuration as taught in my earlier patent, providing for the performance of a valid $K_{Ic}$ test on specimens having smaller dimensions or geometry than could be used in practicing my earlier method. In practicing the method of the present invention, specimens can be utilized that have as small a diameter as 0.9 $(K_{Ic}/\delta_{ys})^2$, with $K_{Ic}$, of course, being the plane strain critical stress intensity factor or fracture toughness, and $\delta_{ys}$ the specimen yield strength in tension. Earlier $K_{Ic}$ measuring techniques require specimens whose dimensions are very large compared to the crack tip non-elastic zone area as called for in ASTM E399-74, entitled "Method for Measuring Plane Strain Fracture Toughness". Therein, it is required that the specimen width and initial crack length to be at least as large as 2.5 $(K_{Ic}/\delta_{ys})^2$. This requirement has heretofore made it difficult or impossible to perform valid ASTM $K_{Ic}$ tests on many important high-toughness materials. The resultant dilemma has led to much interest and effort being expended to find alternative ways of measuring fracture toughness.

The practice of the method of the present invention, like my own and other earlier methods for measuring $K_{Ic}$, defines fracture toughness relative to a steady state crack rather than either an initial crack growth or crack tip instability. Heretofore, a most popular method for measuring plane strain fracture toughness of relatively small samples of ductile materials has been the aforementioned J integral method of $J_{Ic}$. Measured values of $J_{Ic}$ for specimen sizes which heretofore have been too small for linear elastic fracture mechanics determinations have in some cases produced values similar to those obtained for $G_{Ic}$ from sufficiently large specimens where such linear elastic fracture mechanics methods were applicable. Therefore, since the elastic-plastic method of this application also promises to produce $G_{Ic}$ and $K_{Ic}$ values which agree with those obtained from much larger linear elastic fracture mechanics specimens, the following comparison of the present "elastic-plastic" (E-P) method with current ASTM recommended procedures for measuring $J_{Ic}$ is of interest.

| ITEM | $J_{Ic}$ | E-P $K_{Ic}$ |
|---|---|---|
| 1. No. test specimens for each measurement | $\geq 4$ | 1 |
| 2. Fatigue pre-cracking | yes | no |
| 3. Crack length marking via heat tinting | yes | no |
| 4. Multiple-point crack extension measurements | yes | no |
| 5. X-Y plot of load-displacement data | yes | yes |
| 6. Accuracy depends on displacement transducer calibration | yes | no |
| 7. Displacement must be measured at the load line | yes | no |
| 8. Area integration of load-displacement record required | yes | no |
| 9. Computation of a blunting line and a least-squares fit to several data points for each final value | yes | no |

From the above, considering the steps involved in $J_{Ic}$ testing, it will be quite apparent from the following that the determination of $K_{Ic}$ by the elastic-plastic method of the present invention is much simpler and less expensive than a measurement of $J_{Ic}$.

The present method is similar to my earlier $K_{Ic}$ test, but unlike that procedure that assumes a perfectly elastic specimen, the present method recognizes that there may be a non-negligible non-elastic zone existant at and around the crack tip, particularly in a specimen smaller than a certain size. The present method compensates for that non-elastic zone, as will be shown later herein, to provide an accurate determination of the fracture toughness of sizes of specimens that heretofore could not be tested by other than difficult procedures and methods.

Specimen Preparation and Testing

FIG. 1 shows a preferred short rod specimen 10 configuration manufactured from a material to be tested that is slotted longitudinally at 11 so as to leave a V-shaped remainder 12 that has an apex 13 approximately equidistant from specimen 10 sides. In FIG. 1, specimen 10 is shown having a flat face 14 that is preferably normal to slot 11, and has grip grooves 15 machined thereacross in the plane of the slot 11, for mounting in a stiff machine, not shown. Such stiff machine could be like that shown in an earlier patent of the present inventor, U.S. Pat. No. 4,075,884, or like that shown in a pending U.S. patent application by the present inventor, Ser. No. 959,202. A moving apart of grips of such machine, not shown, to load the specimen is illustrated by arrows F in FIG. 1. Under such loading the specimen will initially crack at the apex 13, that crack traveling through the specimen as shown by a darkened area 16, in FIG. 2. Such crack progress therethrough is shown as width "b", with "a" being the distance from the specimen face 14 to the crack front or tip.

Figure 3:
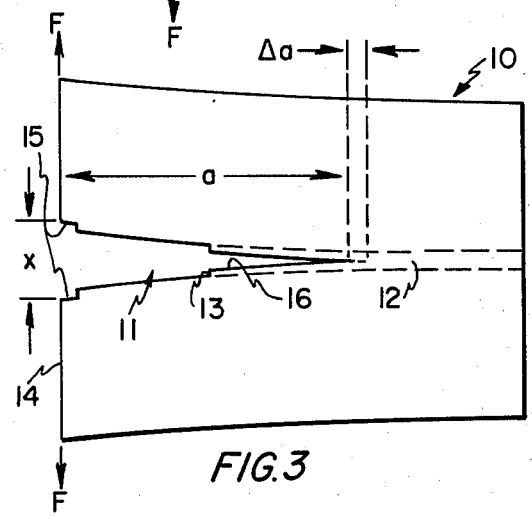
Figure 4:
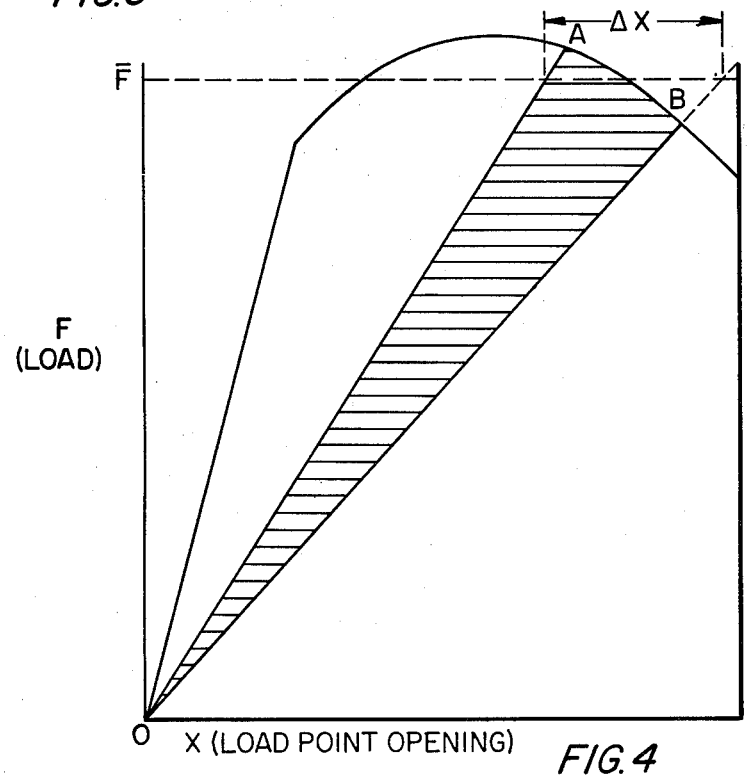

The stiff machine, represented by arrows F in FIGS. 1 and 3, applies a controlled displacement load across specimen 10 that can be discontinued or reduced at a point in specimen test. Thereby, the specimen will not immediately fracture apart as it would if a critical crack location therein were reached and the force not reduced. During such controlled displacement loading, a curve comparing applied load to specimen opening can be constructed like that of FIG. 4, showing the tensile force applied as load F, represented by the vertical ordinate or y axis and the load point opening on the horizontal abscissa or x axis.

A practice of the method of the present invention could be performed on other specimen configurations, not shown, and so the present invention should not be taken as being limited to any particular specimen configuration. Nor should the practice thereof be limited to any particular device or method for applying a load across such specimen. The relation of specimen loading and data collected thereby in practicing the method of the present invention and its use in computing fracture toughness, $K_{Ic}$, of a specimen will be explained in detail in the following section.

Linear Elastic Fracture Mechanics Derivation

Figure 2:
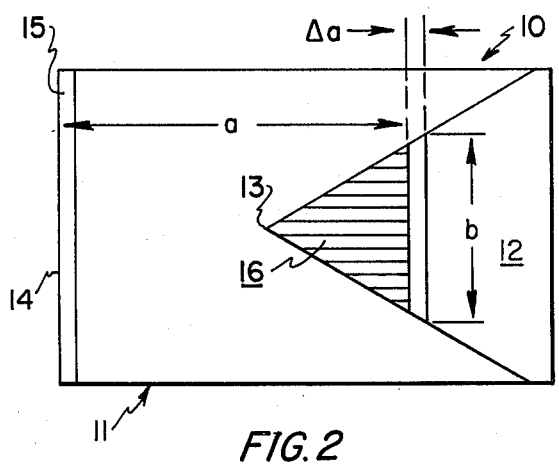

With a material that, when tested, behaves according to linear elastic fracture mechanics standards, which material has been formed into the configuration of the short rod specimen 10, as shown in FIGS. 1 through 3, a slowly increasing load F is provided across the specimen. The load is increased across the specimen 10 until a crack initiates at 13. Crack growth, after reaching a steady state, increases with increasing load, the crack advancing through the V-shaped remainder portion 12 until it reaches a critical crack length $a_c$. The value of the critical crack length, $a_c$, has been found experimentally, and is shown theoretically, to be a constant for a given specimen geometry and loading configuration and is independent of the specimen material so long as the specimen behaves according to linear elastic fracture mechanics principles. A peak load, identified as $F_c$, occurs when the crack passes through $a_c$, and can be used to calculate $K_{Ic}$ or fracture toughness. Of course, after the critical crack length $a_c$ is reached, the loading force required to further advance the crack through the specimen, to split the specimen apart, decreases with an increase in crack length.

The equation for $K_{Ic}$ or fracture toughness is preferably derived using a familiar compliance approach with reference to FIGS. 1–3 as follows: The energy or work, $\Delta W$, required to advance a steady state crack a small distance $\Delta a$ is:

$$\Delta W = G_{Ic} b\, \Delta a, \qquad (1)$$

where: the $G_{Ic}$ is defined as the energy required per unit area swept out by a quasistatically advancing mode I steady-state crack tip in material constrained to plane strain, and b is, of course, the average width of the crack front between a and a+$\Delta a$. Therefrom, the energy or work $\Delta W$ is the irrecoverable work done on the specimen during the test to move the crack a distance $\Delta a$.

Referring to FIGS. 1 and 3, the force F across that specimen causes the specimen across slot 11 to open by an amount x. The graph of FIG. 4 shows the applied load F represented on vertical, ordinate or y axis with opening across the specimen at x shown represented on the horizontal, abscissa or x axis. Shown in the theoretical graph of FIG. 4, before crack initiation, the loading path F versus opening x proceeds as a steep linear elastic slope, and, at the onset of non-linearity, the graph arches over, signifying initiation of a crack at the point or apex 13 of the V-shaped remainder 12. Preferably, the specimen 10 is loaded under controlled displacement conditions until the steady state crack tip configuration is obtained, and until a point shown as A in FIG. 4 is reached, wherefrom the specimen 10 is unloaded. Assuming no crack growth and no non-elastic deformation occurs on unloading, the unloading path would be a straight line to the origin or the intersection of the x and y axes. Such straight path back to origin, of course, assumes that the crack would completely close and that no non-elastic deformation had occurred to prohibit that complete closure, the specimen thereby behaving in accordance with linear elastic fracture machanics principles. Thereafter, the specimen is again loaded and the steady state crack is advanced quasistatically an additional increment, $\Delta a$, as shown in FIGS. 2 and 3. Such crack growth would, of course, be accompanied by an additional load point opening increment such that the loading path would advance to a point shown as B. Thereafter, a subsequent unloading from point B would produce another straight line back to origin, again assuming the specimen exhibits linear elastic fracture mechanics characteristics Therefrom, the irrecoverable work, $\Delta W$, done in advancing the crack the additional distance $\Delta a$, shown in FIGS. 2 and 3, would be the shaded area of the graph of FIG. 4, or the triangle OAB, or:

$$\Delta W = \tfrac{1}{2}\overline{F}\Delta x \quad (2)$$

where, $\overline{F}$ is the average load between A and B, and $\Delta x$ is longitudinal separation of the release points at the average load.

Additional to determining the average load between points A and B, to relate that load to a specimen cracking, it is necessary to determine the incremental change in elastic compliance as results from loading from A to B, the formula for which incremental change in elastic compliance is:

$$\Delta c = \frac{\Delta x}{\overline{F}} \quad (3)$$

From the above equation, $\Delta x$ can be eliminated by the inclusion of the above equation (3) in equation (2), resulting in:

$$\Delta W = \tfrac{1}{2}\overline{F}^2 \Delta c, \quad (4)$$

and including equation (4) with equation (1), taking the limit as $\Delta c$ and $\Delta a$ approach zero, results in $$G_{Ic} = \frac{F^2}{2b}\left(\frac{dc}{da}\right), \quad (5)$$

$G_{Ic}$, of course, is the energy required per unit area swept out by a quasistatic steady state crack tip in a plane-strain stress field, and b, F and dc/da are evaluated at the crack length, a, at which the incremental crack advance took place, as shown best in FIGS. 1, 2 and 3. The above equation (5) is not new and was shown in an article by Irwin, G. R. and Kies, J. E., entitled "Critical Energy Rate Analysis of Fracture Strength", cited in Weld. J. 33, 193, 1954, and cited in my earlier mentioned U.S. Pat. No. 4,116,049.

Referring to the above equation (5), in order to cast the equation in terms of the critical stress intensity factor, $K_{Ic}$, the plane strain equation relating $G_{Ic}$ and $K_{Ic}$ is used that was also shown in my above cited U.S. Patent, or:

$$G_{Ic} = K_{Ic}^2 \frac{(1-\nu^2)}{E}. \quad (6)$$

Herein, E is elastic modulus and $\nu$ is Poisson's ratio. Therefrom, equation (6), after rearrangement, becomes:

$$K_{Ic} = \frac{F}{B^{3/2}(1-\nu^2)^{\frac{1}{2}}} f(a/B) \quad (7)$$

where B is the specimen diameter, and $$f(a/B) = \left(\frac{B\, d(cEB)}{2b\, d(a/b)}\right)^{\frac{1}{2}}. \quad (8)$$

Assuming that the scaled crack position, $a_c/B$, whereat the peak load or $F_c$ is encountered, is a constant and, or course, assuming that linear elastic fracture mechanics conditions prevail, the value of f(a/B) in equation (7) above, at the time the maximum load, $F_c$, is reached, is a constant, therefrom $A = f(a_c/B)$. Therefore, $$K_{Ic} = \frac{AF_c}{B^{3/2}(1-\nu^2)^{\frac{1}{2}}}, \quad (9)$$

or, by following custom in replacing the Poisson's ratio term with unity, we have $$K_{Ic} = \frac{AF_c}{B^{3/2}}. \quad (10)$$

Equations (9) and (10) would also apply, of course, for any known crack length other than $a_c$, provided that the load at that known crack length were substituted for $F_c$, and provided that the constant A is re-evaluated to correspond to that known crack length.

Equations (9) and (10), obviously, are much more simple to work with than former formulas for determining $K_{Ic}$ since a fourth-order polynomial is replaced by the dimensionless constant A. In addition, no measurement of crack length is required and fatigue pre-cracking of the short rod specimen is generally not necessary. In practice, the value of A for a calibrated short-rod specimen configuration has been found to be approximately 20.8.

The above derivation, of course, assumes the specimen will behave according to linear elastic fracture mehanics principles, which assumption has been found to be correct or essentially correct for specimens above certain minimum sizes. However, as the size decreases, specimens tend not to act or behave elastically. Specifically, a plastic zone or a "process" zone at the tip of the crack or crack face interferes with the return of the specimen to its original configuration when loading is discontinued.

Figure 5:
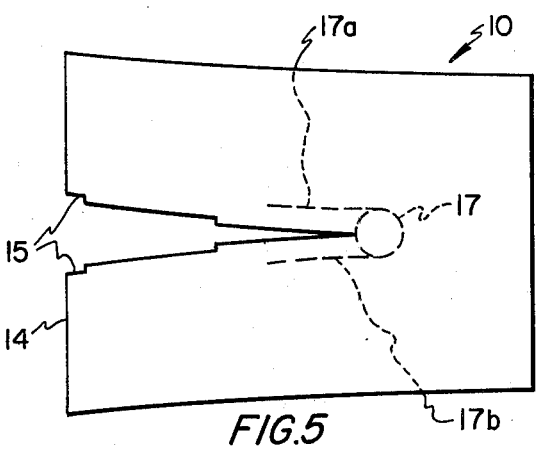

In FIG. 5, specimen 10 is shown as including a non-negligible non-elastic zone represented by a broken circle forward of the crack face, with broken lines 17a and 17b showing the wake of that anelastic zone as the crack progresses through the specimen. The present invention, unlike prior methods, including my own prior method, considers and allows for that non-elastic zone, or its presence and effect on the elasticity of the specimen, in determining specimen $K_{Ic}$. Hereinbelow is a discussion of that derivation.

Elastic-Plastic Derivation

Figures 6, 7, 8:
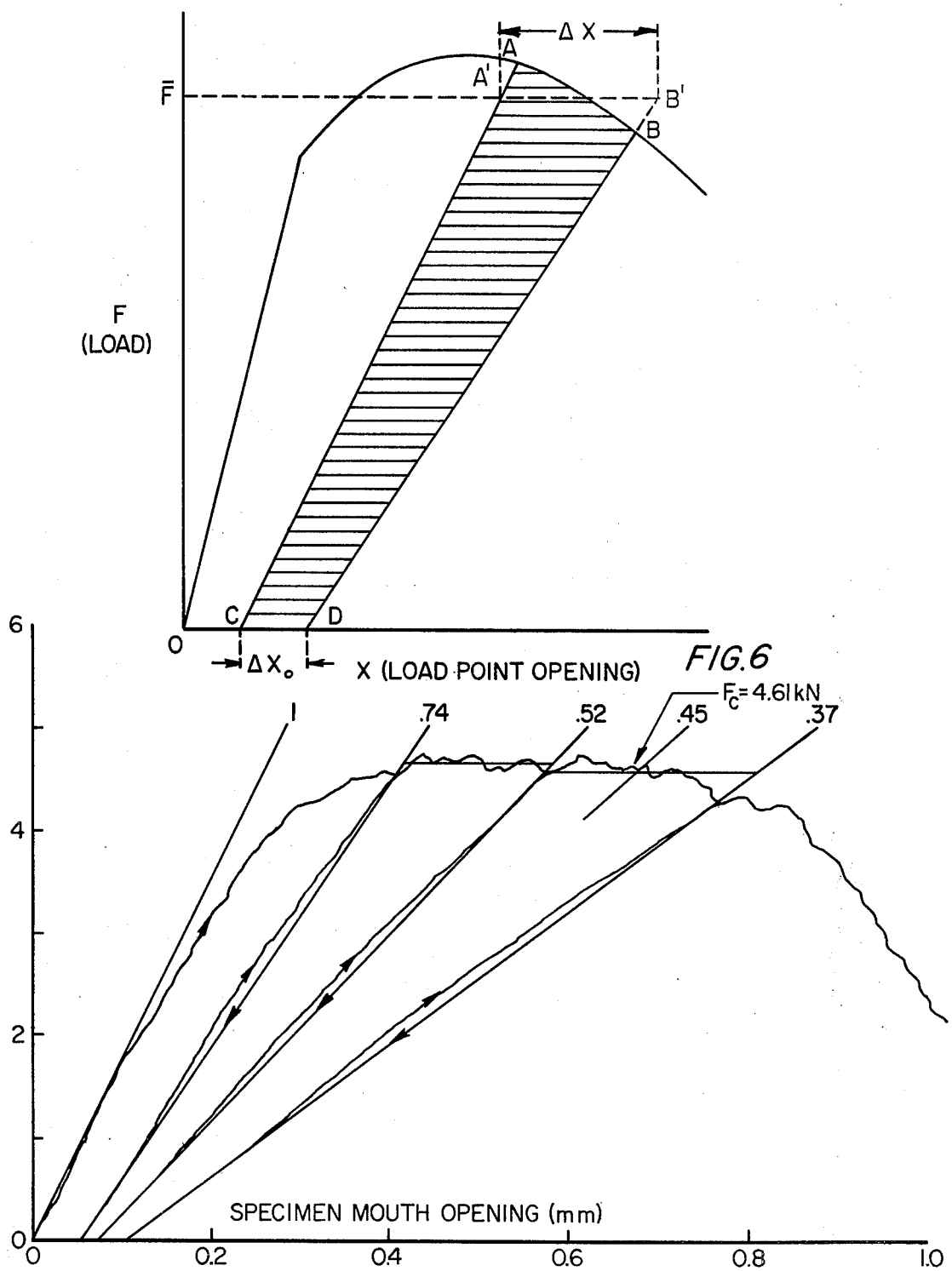

In FIG. 6 is shown a graph that is essentially like the graph of FIG. 4 for a specimen 10 subject to loading. As has been earlier described, the vertical, ordinate or y axis thereof reflects specimen tensile loading and the horizontal, abscissa or x axis reflects load point opening. The graph of FIG. 6, however, shows the load path upon load removal from the specimen as not returning to the point or origin or intersection of the x and y axes. Rather, the unloading path leads to a point forward of the origin on the x axis, which point is dependent upon the amount of specimen cracking and non-elastic deformation that has taken place, as will be described hereinbelow.

Shown in FIG. 6, specimen loading commences at point O. Therefrom, specimen 10 is loaded to some point A (where steady state crack tip conditions have been obtained), and the specimen is then unloaded. If, as has been described, the specimen 10 exhibits linear elastic behavior, the unloading path should return to the origin O. However, if non-elastic deformation has occurred, that unloading path will no longer travel back to the origin. Rather, it will terminate in some offset point on the x axis, at zero loading, shown as C, in FIG. 6. Nevertheless, the unloading path will be a straight line, if no crack growth and negligible non-elastic deformation occurs during the unloading. Thereafter, the specimen 10 is preferably reloaded as shown in FIG. 6, the specimen cracking to point B with the additional quasistatic crack advance shown as $\Delta a$. In a subsequent unloading the load path travels to point D, forward of point C on the x axis. The distance between points C and D shown as $\Delta x_o$ is the additional residual specimen load point opening due to loading between A and B. Therefrom, the additional irrecoverable work done in loading the specimen from A to B is the shaded area CABD in FIG. 6.

It can be assumed that the work per unit area swept out by the crack front or tip is still the same material constant, $G_{Ic}$, as in the linear elastic fracture mechanics case, although the size of the crack front non-elastic zone is large enough to prevent the specimen, as a whole, from behaving entirely elastically. Therefore, the area shown in FIG. 6 identified as CABD reflects the work $\Delta W$ in increasing the fracture length by an amount $\Delta a$ in loading from A to B and is approximated by the trapezoidal area CA'B'D, points A' and B' reflective of the change in load-point opening at the average load $\overline{F}$, which $\Delta W$ is given exactly by the equation:

$$\Delta W = \tfrac{1}{2}(1+p)\overline{F}\Delta x. \tag{11}$$

Therein, p is defined as the ratio of the two bases of the trapezoid CA'B'D, $\Delta x_o$ and $\Delta x$, with $\Delta x_o$, of course, being the distance between CB on the horizontal axis, or, $$p \equiv \frac{\Delta x_o}{\Delta x} \tag{12}$$

The above parameter p can be interpreted as the degree of "plasticity" exhibited by the specimen between two points on a loading curve reflective of crack growth. Should $p=0$, i.e., $\Delta x_o = 0$, that would mean that the specimen suffered no additional non-elastic bending during the loading from A to B. Whereas, should the value of $p=1$, ($\Delta x_o = \Delta x$), this would imply that there is no change in the release path slope, meaning that no crack growth had occurred, and that $\Delta x$ is entirely attributable to non-elastic deformation of the specimen. From the above, it should be obvious that p can also be measured experimentally by making a plot of load vs. load-point opening of the specimen, and including the relaxation slopes from the points A and B toward the horizontal axis. The values of $\Delta x$ and $\Delta x_o$ can then be determined graphically, as shown in FIG. 6.

To determine the compliance change between the two relaxation paths we add to the equation (3) cited hereinabove as $\Delta c = (\Delta x/\overline{F})$ the change in compliance as determined from the graph of FIG. 6 including the quantity of (1-p), or:

$$\Delta c = (1-p)\frac{\Delta x}{\overline{F}}. \tag{13}$$

Then as was done with equation (4), by eliminating $\Delta x$ the following formula is derived:

$$\Delta W = \tfrac{1}{2}\left(\frac{1+p}{1-p}\right)\overline{F}^2\Delta c \tag{14}$$

and by equating equations (1) and (14), and taking the limit as $\Delta c$ and $\Delta a$ approach zero, then:

$$G_{Ic} = \left(\frac{1+p}{1-p}\right)\frac{F^2}{2b}\left(\frac{dc}{da}\right). \tag{15}$$

Equation (15) is therefore a new generalized compliance relation that is identical to equation (5) in the linear elastic fracture mechanics derivation except for the inclusdion of the plasticity factor $(1+p)/(1-p)$. Thus, the elastic-plastic Equation for $G_{Ic}$ becomes equal to the linear elastic fracture mechanics equation when the specimen plasticity, p, is zero.

Equation (15), of course, is like the equation (5) shown earlier herein but, additionally, takes into account specimen plasticity. Therefrom, in terms of the critical stress intensity factor, $K_{Ic}$, the plane strain equation relating $G_{Ic}$ and $K_{Ic}$ assumes that $G_{Ic}$ is the same material property that would have been measured in a linear elastic fracture mechanics test on the same material using whatever specimen size would qualify to meet the linear elastic fracture mechanics criterion. Therefore, from the above, and taking into account specimen plasticity, it is valid to apply the linear elastic fracture mechanics eqaution to translate $G_{Ic}$ to $K_{Ic}$. Applying this translation to $G_{Ic}$, then:

$$K_{Ic} = \left(\frac{1+p}{1-p}\right)^{\frac{1}{2}} K_Q, \tag{16}$$

where $K_Q$ is the value of the stress intensity factor that would be obtained from the linear elastic fracture mechanics analysis equation (9), and ignoring the presence of non-elastic effects. A distinction between $K_Q$ for specimens exhibiting perfect elasticity versus one where anelasticity is present, however, is that while $F_c$ is always the peak load in a truly linear elastic fracture mechanics test, it may not be the peak load in non-elastic specimens. Therefore, the initial elastic loading slope and the two unloading slopes from points A and B of FIG. 6 can be used to estimate the point on the loading curve where the crack passes through the critical crack location, $a_c$. The elastic relaxation slope when the crack is at $a_c$ is about half of the initial elastic loading slope. Thus, $F_c$ can usually be obtained by interpolation between points A and B.

As the specimen plasticity, p, will generally not be a constant, but will vary somewhat with the crack length a, the experimentally determined p will actually be the average p between points A and B of FIG. 6. To obtain the best accuracy, therefore, points A and B should bracket the crack length which is used to calculate the fracture toughness.

Experimental Results

FIG. 7 shows a graph representation of specimen loading vs. specimen mouth opening of an experiment conducted on a single 22 mm diameter specimen. The table of FIG. 8 shows data from experiments conducted on different specimen diameters including the experiment represented by the graph of FIG. 7 and on other specimens ranging in size from 12.7 mm to 63.5 mm. The table reflects the number of tests conducted on such specimens, records the average $K_Q$, plasticity p, $K_{Ic}$ and the standard deviation for specimens of the same diameter. The table is a summary of the tests performed on drawn rod 6061-T651 aluminum specimens, where the specimen lengths were always 1.5 times the specimen diameter. Each specimen was machined from the center-most section of the rod to be tested with the axis of the specimen running along the axis of the original rod. The slot widths were machined to be 2 to 3 percent of the specimen diameter.

Specimen loading for each of these experiments was accomplished by pulling across the specimen at grips fitted into appropriate grip grooves formed in a face of each specimen. A clip gage was used to monitor the specimen mouth opening, and a plot was made of the applied load vs. the specimen mouth opening. FIG. 7 is an exact reproduction of one such plot exceping the specimen in practice is not taken to a zero loading so as to avoid specimen displacement on grip jaws, now shown, and so the unloading path from approximately 1 on the y scale is extrapolated to an x axis intercept. In each experiment a specimen was unloaded three times and three release slopes were drawn instead of the two slopes shown in FIGS. 4 and 6. The additional release slope allowed for a second measurement of plasticity p, at a different average crack length, which measurement indicated the degree of variation of p with crack length.

The linear unloading slopes shown in FIG. 7, as stated hereinabove, have been extrapolated to a zero-load axis for the graphical determination of $\Delta x_o$ and the horizontal lines are drawn to represent the average load between the unloading slopes such that the plasticity, p, which is the ratio $\Delta x_o / \Delta x$, can be determined. The average values of plasticity, p, for each specimen size are listed in the table of FIG. 8, showing an average p decrease consistant with increasing specimen size, as would be expected.

The value of $K_Q$ was calculated from equation (9), substituting, of course, $K_Q$ for $K_{Ic}$, with load $F_c$ the load on the specimen when the crack is at the linear elastic fracture mechanics critical crack location, $a_c$. In a non-elastic specimen, as stated earlier herein, the load $F_c$ to advance the crack through the critical crack location $a_c$ may not be the peak load as in a linear elastic fracture mechanics case, and so the present experiment, to determine $F_c$, makes use of the fact that the specimen's elastic unloading slope, when the curve is at $a_c$, is of the order of fifty percent of the initial elastic loading slope. Shown in FIG. 7, the slope ratio corresponding to a crack length of $a_c$ is about 0.45, whereat the $F_c$ is 4.61 kN. The values of the slope ratios can be seen at the tops of the extrapolated slopes in FIG. 7 and therefrom, as outlined hereinabove, by interpolation, the value of $F_c$ at the desired slope ratio was found. Therefore, having determined $F_c$, the $K_Q$ can be calculated using equation (9) and the $K_{Ic}$ will then follow using equation (16).

The table of FIG. 8 lists the average values of $K_Q$ and $K_{Ic}$ obtained from various specimen sizes together with the number of experiments conducted to derive this average and the standard deviation. While $K_Q$ has no physical significance by itself, it is an interesting parameter to compare with $K_{Ic}$ since it shows the effect of the plasticity of the specimen.

The standard deviations shown in the table of FIG. 8 were three percent (3%) or less for all but the 38.1 mm specimens, for which specimens the standard deviation was four point five percent (4.5%). It should be noted that seven tests were conducted on these particular 38.1 mm specimens, with five of the specimens machined from the very end of the original 63.5 mm diameter rod. The $K_{Ic}$'s of these specimens averaged only 31.9 MPa$\sqrt{m}$, while the other two 38.1 mm specimens that were machined from a different part of the original rod had $K_{Ic}$'s averaging 34.1 MPa$\sqrt{m}$. Thus, it may well be that the greater standard deviations and slightly lower $K_{Ic}$ obtained from the 38.1 mm specimens could have been caused by a small decrease in toughness near the end of the original rod. Even discounting this possibility, the standard deviation of the $K_{Ic}$ averages for the four specimen sizes is only 2.9 percent. Moreover, no experimentally significant trend of increasing or decreasing $K_{Ic}$ values with specimen diameter can be seen from the table. Therefore, it is reasonable to conclude that these experiments show that the method of the present invention can be practiced with acceptable results on 6061-T651 aluminum specimens having as small a diameter as 12.7 mm, producing an accurate fracture toughness determination. Consider that the minimum ASTM specimen thickness for this material for performing $K_{Ic}$ testing by former methods is approximately 36 mm, the weight of a minimum-size short rod specimen that can be used in practicing the method of the present invention is only about one percent of the weight of a minimum-size ASTM specimen.

The method of the present invention has also been used to measure the fracture toughness of limestone rock from the State of Indiana. Results were produced similar to those cited hereinabove for 6061-T651 aluminum, that is, a specimen size dependence was present if linear elastic fracture mechanics conditions were assumed, but the measurement and application of the plasticity factor thereto of the present invention provided valid $K_{Ic}$'s for much smaller specimens.

From the theoretical discussion and the experimental data presented hereinabove, it should be obvious that the practice of the method of the present invention provides a number of advantages over former methods, one being that no calibration of a specimen mouth opening transducer is necessary since p is the ratio of two mouth opening displacements and is therefore independent of such calibration constant. In practice, specimen mouth opening need not even be measured at the load line—as any measurement which is proportional to the displacement of the load line provide the same results. Second, the load, $F_c$, is determined by loading and unloading slope ratios, making it also independent of the mouth opening transducer calibration.

Although preferred procedures for practicing the method of my invention have been shown and described herein, it should be understood that the present disclosure is made by way of example and that variations are possible without departing from the subject matter coming within the scope of the following claims, which subject matter I regard as my invention.

I claim:

1. A method for determining plane strain fracture toughness of non-elastic fracture mechanics specimens comprising the steps of, forming a slotted specimen of a material leaving an internal "v" shape as a remainder therein;

applying an incrementally increasing opening across said specimen so as to cause a crack to initiate and propagate in essentially plane strain conditions along a predetermined path through said specimen;

recording and comparing specimen loading against specimen opening displacement;

performing and recording at least two unloadings from different crack lengths;

determining specimen plasticity by dividing the difference in the residual zero-load mouth opening between the two unloading paths by the difference in mouth opening between the unloading paths at the average load;

determining the load required to advance the crack at a known crack location in said specimen; and computing said material's fracture toughness from the load required to advance the crack at the known crack location in said specimen, and from considerations of said specimen size, plasticity, and geometry.

2. A method as defined in claim 1, further including the step of,
unloading the specimen from crack lengths that bracket the known crack location.

3. A method as defined in claim 1, further including the step of,
recording specimen loading on a graph of specimen loading along a vertical axis and specimen mouth opening along a horizontal axis.

4. A method as defined in claim 1, further including the step of
stabilizing crack growth to a quasistatic steady state prior to unloading.

5. A method of defined in claim 1, wherein
in computing said specimen material fracture toughness which is also the specimen material critical stress intensity factor, "$K_{Ic}$", is equal to a dimensionless constant "A" for the specimen's geometric configuration times the load at the specimen's critical crack location $F_c$, divided by a characteristic dimension of the specimen which identifies its physical size "B" to the 3/2 power, times the square root of one plus specimen plasticity, "p", over one minus specimen plasticity, "p", $$K_{Ic} = \frac{AF_c}{B^{3/2}} \left( \frac{1+p}{1-p} \right)^{\frac{1}{2}}.$$

6. A method as defined in claim 5, wherein the term $$\left( \frac{1+p}{1-p} \right)^{\frac{1}{2}}$$

is approximated as (1+p) for small values of p.

7. A method as defined in claim 5, further including in computing the fracture toughness of the specimen material the square root of one minus Poisson's ratio squared, $$K_{Ic} = \frac{AF_c}{B^{3/2}(1-\nu^2)^{\frac{1}{2}}} \left( \frac{1+p}{1-p} \right)^{\frac{1}{2}}$$

8. A method as defined in claim 6, wherein the term $$\left( \frac{1+p}{1-p} \right)^{\frac{1}{2}}$$

is approximated as (1+p) for small values of p.

9. A method as defined in claim 1, wherein the difference in the residual zero-load mouth opening between two unloading paths is determined from partial unloading paths in which the load is not fully removed.

* * * * *